United States Patent
DeSimone et al.

(10) Patent No.: US 6,358,949 B1
(45) Date of Patent: Mar. 19, 2002

(54) ARYL AND HETROARYL FUSED AMINOALKYL-IMIDAZOLE DERIVATIVES: SELECTIVE MODULATORS OF BRADYKININ $B_2$ RECEPTORS

(75) Inventors: Robert W. DeSimone, Durham; Alan Hutchison, Madison; Kenneth Shaw, Weston; George D. Maynard, Clinton; John M. Peterson, Madison; Richard Lew, Hamden; Harry L. Brielmann, Guilford, all of CT (US)

(73) Assignee: Neurogen Corporation, Branford, CT (US)

( * ) Notice: Subject to any disclaimer, the term of this patent is extended or adjusted under 35 U.S.C. 154(b) by 0 days.

(21) Appl. No.: 09/540,580

(22) Filed: Mar. 31, 2000

Related U.S. Application Data

(60) Provisional application No. 60/127,505, filed on Apr. 2, 1999.

(51) Int. Cl.[7] .................. A61K 31/5377; C07D 413/12
(52) U.S. Cl. .................. 514/234.5; 544/139; 544/370; 546/118; 546/199; 546/273.4; 548/253; 548/306.1; 548/309.7
(58) Field of Search ...................... 544/139; 548/309.7; 514/234.5

(56) References Cited

U.S. PATENT DOCUMENTS

| | | |
|---|---|---|
| 3,255,202 A | 6/1966 | Johnson |
| 3,995,044 A | 11/1976 | Kabbe et al. |

FOREIGN PATENT DOCUMENTS

| | | |
|---|---|---|
| EP | 0 882 718 A | 12/1998 |
| WO | WO 96/00730 | 1/1996 |
| WO | WO 96/33194 | 10/1996 |
| WO | WO 97/24119 | 7/1997 |
| WO | WO 98/17651 | 4/1998 |

Primary Examiner—Robert W. Ramsuer
(74) Attorney, Agent, or Firm—McDonnell Boehnen Hulbert & Berghoff

(57) ABSTRACT

Disclosed are compounds of the formula:

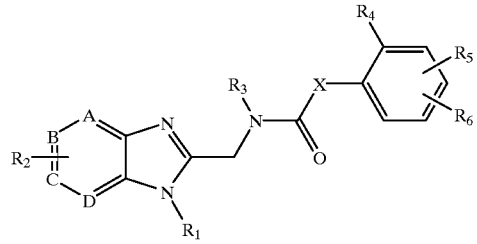

or the pharmaceutically acceptable non-toxic salts thereof wherein:

A, B, C and D are N or CH;

X is a bond or (un)substituted $CH_2$;

$R_1$ is lower alkenyl or (un)substituted lower alkyl;

$R_3$ is lower alkyl; and $R_2$, $R_4$, $R_5$, and $R_6$ are variables defined herein;

which compounds are useful in the diagnosis and treatment of renal diseases, heart failure, hypertension, Meniere's disease, vaginal inflammation and pain, peripheral circulatory disorders, climacteric disturbance, retinochoroidal circulatroy disorders, myocardial ischemia, myocardial infarction, postmyocardial infarction syndrome, angina pectoris, restenosis after percutaneous transluminal coronary angioplasty, hepatitis, liver cirrhosis, pancreatitis, ileus, diabetes, diabetic complications, male infertility or glaucoma, or for the increase of permeability of blood-brain barrier, pain, asthma, and rhinitis.

56 Claims, No Drawings

# ARYL AND HETROARYL FUSED AMINOALKYL-IMIDAZOLE DERIVATIVES: SELECTIVE MODULATORS OF BRADYKININ $B_2$ RECEPTORS

This application claims the benefit of U.S. Provisional Application No. 60/127,505, filed Apr. 2, 1999.

BACKGROUND OF THE INVENTION

1. Field of the Invention

This invention relates to aryl and heteroaryl fused aminoalkylimidazole derivatives which, when appropriately substituted, are selective modulators of Bradykinin $B_2$ receptors. This invention also relates to pharmaceutical compositions comprising such compounds. It further relates to the use of such compounds in treating a variety of central and peripheral disorders. Additionally, compounds of this invention are useful as positive controls in assays for BK-2 receptor activity and when appropriately labeled as probes for the localization of BK-2 receptors in tissue sections.

2. Background

Bradykinin (BK), a nonapeptide, and the closely related decapeptide kallidin (Lys-BK), are produced by proteolytic cleavage of high molecular weight kininogen by plasma kallikreins (Bhoola et al., Pharmacol. Rev. 1992, 1–80; Regoli et al. Pharmacol. Rev. 1980 1–46; Bathon & Proud, Ann. Rev. Pharmac. Toxic. 1991, 129–162). The effects of bradykinin and kallidin are mediated by specific seven transmembrane G-proteirn coupled receptors.

The existence of two bradykinin receptor subtypes was initially proposed by Regoli and Barabe (Pharmacol. Rev., 1980, 1–46) and this hypothesis had been unequivocally confirmed within the last six years. The expression and cloning of a rat bradykinin receptor, now known to be a BK-2 receptor, was first reported by McEachern et al. (PNAS 1991, 88(17):7724–7728). Hess, et al. (Biochem Biophys. Res. Commun. 1992, 260–268) reported the cloning and pharmacological characterization of a human BK-2 receptor. Menke, et al. (J. Biol. Chem. 1994, 21583–21586) describes the expression and cloning of a human bradykinin ($B_1$) receptor.

Both BK and kallidin activate the $B_2$ receptor while only kallidin is active at the $B_1$ receptor. However, both compounds are rapidly cleaved to produce $B_1$ receptor agonists, and then further degraded by kinases to produce inactive peptides. The instability of BK and kallidin suggests that these peptides act. locally. Both receptors are expressed in a number of peripheral tissues as well as in the CNS.

The $B_2$ receptor is expressed constitutively in a variety of: tissues (Regoli et al., Eur. J. Pharmacol., 1981, 105–115) and accounts for the majority of the acute pharmacological effects of bradykinin. The $B_1$ receptor is inducibly expressed (Regoli et al., Eur. J. Pharmacol., 1981, 105–115; Deblois et al., Immunopharmacology, 1989, 187–98; Marceau, Immunopharmacology, 1995, 1–26.) and appears to act predominantly in, pathophysiological conditions (Dray and Perkins, J. Neurophysiol., 1993, 256–272). The BK-1 receptor has been especially implicated in persistent hyperalgesia and chronic inflammation.

Bradykinin is an effector of a number of inflammatory responses including bronchoconstriction, plasma extravasation, release of prostaglandins/leukotrienes, smooth muscle contraction/relaxation and nociception (Burch et al., Med. Res. Rev. 1990, 237–269). Bradykinin and the related peptide kallidin have been implicated in a number of disease conditions, including but not limited to pain (Whalley et al., Naunyn. Schmiedeberg's Arch. Pharmc., 1987, 652–655), rhinitis, anaphylaxis, inflammatory bowel disease, vascular permeability (Schachter et al., Br. J. Pharmac., 1987, 851–855; Whalley et al., Naunyn Schmiedeberg's Arch. Pharmc., 1987, 430–433), algesia, vasodilataion, inflammatory response (Burch & De Haas, Naunyn Schmiedeberg's Arch. Pharmc. 1990, 189–193), hypotension associated with sepsis (Sharma et al., Agents Actions, 1992, 258–269), bronchopulmonary disorders including asthma (Jin et al., Br. J. Pharmac., 1989, 598–602), and increased cell proliferation. Antagonists of the BK-2 receptor are useful in treating these conditions. Additionally bradykinin has been implicated in increased glucose uptake, and decreased blood glucose concentration (Henriksen et al., Diabetes, 1996, S125–S128; Yang et al., J Pharmacol. Exp. Ther., 1997, 1247–1252). Therefore agonists of the BK-2 receptor may be useful in the treatment of Type II diabetes. Unterberg et al. (J Cereb. Blood Flow Metab., 1984, 574–585) report an increased permeability of the blood-brain barrier due to bradykinin. Thus, agonists of the BK-2 receptor could also be used to increase the brain levels of pharmaceutical compounds used to treat central nervous system disorders when administered with these compounds. Therefore, compounds that modulate the bradykinin $B_2$ (BK-2) receptor as agonists or antagonists would have considerable therapeutic benefit.

A number of tissues and cultured cell lines has been assessed for the presence of bradykinin receptors using radiolabeled bradykinin or a radiolabeled bradykinin analogue as a probe (See Hall, Gen. Pharma., 1997, 28: 1–6, for a compilation of such studies.). Although bradykinin and its analogues exhibit high affinity for bradykinin receptors there are some difficulties in using these ligands as receptor localization probes. Bradykinin binds to both BK-1 and BK-2 receptors and therefore cannot be used to distinguish receptor subtypes. Also bradykinin and many of its peptide analogues are susceptible to rapid degradation by kininases, leading to experimental difficulties. Nonpeptidic ligands are not susceptible to kininase activity. Therefore, small molecules that bind with high affinity and high selectivity to BK-2 receptors are especially desirable tools for BK-2 localization studies.

SUMMARY OF THE INVENTION

This invention provides compounds of Formula I (shown below) and pharmaceutical compositions comprising compounds of Formula I. Preferred compounds of the invention exhibit high selectivity for G-coupled protein receptors, especially bradykinin $B_2$ receptors. Preferred compounds of Formula I also bind with high affinity to these receptors.

The invention further provides methods of treating patients suffering from certain inflammatory disorders and other conditions mediated by bradykinin. The invention also provides methods of treating patients (humans and non-humans) suffering from conditions in which agonism of the BK-2 receptor may prove beneficial. Treatment of humans, domesticated companion animals (pets) or livestock animals suffering such conditions with art effective amount of a compound of the invention is contemplated by the invention.

In a separate aspect, the invention provides methods of using compounds of this invention as positive controls in assays for BK-2 receptor activity and using appropriately labeled compounds of the invention as probes for the localization of BK-2 receptors in tissue sections.

Accordingly, in one aspect, the invention is directed to compounds of Formula I:

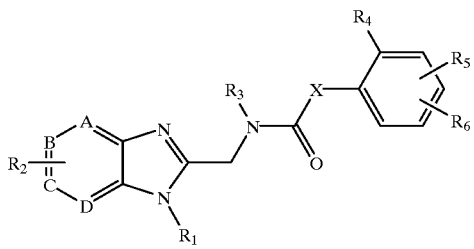

wherein:
R$_1$ is not 3-fluorobenzyl and represents
  (i) (C$_2$–C$_6$)alkenyl; or
  (ii) R$_1$ represents aryl(C$_1$–C$_6$)alkyl or heteroaryl (C$_1$–C$_6$)alkyl, where the ring portion of each is optionally substituted with one, two or three groups independently selected from halogen, nitro, trifluoromethyl, trifluoromethoxy, cyano, hydroxy, (C$_1$–C$_6$)alkyl, hydroxy(C$_1$–C$_6$)alkyl, amino, mono- or di(C$_1$–C$_6$)alkylamino, amino(C$_1$–C$_6$)alkyl, mono- or di(C$_1$–C$_6$)alkylamino(C$_1$–C$_6$)alkyl, mono- or di(C$_1$–C$_6$)alkylamino(C$_1$–C$_6$)alkoxy, or
  (iii) OR$_7$, O(CH$_2$)$_n$C(O)R$_7$, O(CH$_2$)$_n$NR$_7$R$_8$, O(CH$_2$)$_n$CO$_2$R$_7$, NR$_7$COR$_8$, COR$_7$, CONR$_7$R$_8$ or CO$_2$R$_7$ where
    n=1, 2, 3, or 4 and
    R$_7$ and R$_8$ are the same or different and represent hydrogen, SO$_2$Me, or (C$_1$–C$_6$)alkyl; or
    R$_7$ and R$_8$ together with the nitrogen to which they are attached form a 5, 6 or 7 membered carbocyclic ring where up to two of the members in the ring are optionally hetero atoms selected from oxygen, sulfur and nitrogen, and where each member is optionally substituted with (C$_1$–C$_6$)alkyl;
R$_2$ represents
  hydrogen, hydroxy, halogen, trifluoromethyl, trifluoromethoxy, amino(C$_1$–C$_6$)alkyl, mono- or di(C$_1$–C$_6$)alkylamino(C$_1$–C$_6$), mono- or di(C$_1$–C$_6$)alkylamino(C$_1$–C$_6$)alkoxy; or
  OR$_7$, O(CH$_2$)$_n$C(O)R$_7$, O(CH$_2$)$_n$NR$_7$R$_8$, O(CH$_2$)$_n$CO$_2$R$_7$, NR$_7$COR$_8$, COR$_7$, CONR$_7$R$_8$ or CO$_2$R$_7$ where
    n=1, 2, 3, or 4; and
    R$_7$ and R$_8$ are the same or different and represent hydrogen, SO$_2$Me, or (C$_1$–C$_6$)alkyl; or
    R$_7$ and R$_8$ together with the nitrogen to which they are attached form a 5, 6 or 7 membered carbocyclic ring where up to two of the members are optionally hetero atoms selected from oxygen, sulfur and nitrogen, and where each member is optionally substituted with (C$_1$–C$_6$)alkyl;
R$_3$ represents (C$_1$–C$_6$)alkyl;
R$_4$ represents halogen or trifluoromethyl;
R$_5$ and R$_6$ are the same or different and represent hydrogen, trifluoromethyl, trifluoromethoxy, cyano, (C$_1$–C$_6$)alkyl, halogen, (C$_1$–C$_6$)alkylamino(C$_1$–C$_6$)alkyl, mono or di(C$_1$–C$_6$)alkylamino(C$_1$–C$_6$), or mono- or di(C$_1$–C$_6$)alkylamino(C$_1$–C$_6$)alkoxy; or
R$_4$ and R$_5$ together with the carbon atoms to which they are attached form a 5 or 6 membered aromatic ring which is optionally substituted with one or two groups independently selected from
  halogen, nitro, trifluoromethyl, cyano, hydroxy, (C$_1$–C$_6$)alkyl, amino, or mono- or di(C$_1$–C$_6$)alkylamino; or
  OR$_7$, O(CH$_2$)$_n$C(O)R$_7$, O(CH$_2$)$_n$NR$_7$R$_8$, O(CH$_2$)$_n$CO$_2$R$_7$, NR$_7$COR$_8$, COR$_7$, CONR$_7$R$_8$ or CO$_2$R$_7$ where
    n=1, 2, 3, or 4; and
    R$_7$ and R$_8$ are the same or different and represent hydrogen, SO$_2$Me, or (C$_1$–C$_6$)alkyl; or
    R$_7$ and R$_8$ together with the nitrogen to which they are attached form a 5, 6 or 7 membered carbocyclic ring where up to two of the members are optionally hetero atoms selected from oxygen, sulfur and nitrogen, and where each member is optionally substituted with (C$_1$–C$_6$)alkyl;
X represents a bond or CH$_2$, where the CH$_2$ is optionally mono- or disubstituted with a (C$_1$–C$_6$)alkyl or (C$_1$–C$_6$)alkoxy; and
A, B, C and D are the same or different and represent CH or N with the proviso that not more than two of A, B, C and D represent N.

Preferred compounds of the inventions are modulators of G-coupled protein receptors, especially BK-2 receptors. These compounds are therefore useful in the diagnosis and treatment of renal diseases, heart failure, hypertension, Meniere's disease, vaginal inflammation and pain, peripheral circulatory disorders, climacteric disturbance, retinochoroidal circulatroy disorders, myocardial ischemia, myocardial infarction, postmyocardial infarction syndrome, angina pectoris, restenosis after percutaneous transluminal coronary angioplasty, hepatitis, liver cirrhosis, pancreatitis, ileus, diabetes, diabetic complications, male infertility or glaucoma, or for the increase of permeability of blood-brain barrier, pain, asthma and rhinitis.

In another aspect, the invention provides methods for treating and/or preventing the above-listed disorders, which methods comprise administration to a patient in need thereof of an effective amount of a compound of Formula I.

In yet another aspect, the invention provides intermediates useful in the preparation of the compounds of Formula I.

DETAILED DESCRIPTION OF THE INVENTION

The compounds encompassed by the instant invention are represented by general Formula I set forth above and include the pharmaceutically acceptable non-toxic salts thereof.

In addition, the present invention also encompasses compounds of Formula II

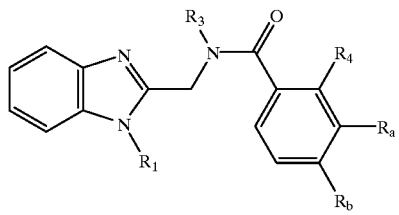

wherein R$_1$ is as defined above for Formula I; and
R$_3$ is C$_3$–C$_6$ alkyl, preferably n-butyl, isoamyl, or n-pentyl;
R$_4$ is chloro or fluoro; and
R$_a$ and R$_b$ independently represent hydrogen or C$_1$–C$_6$ alkoxy.

More preferred compounds of Formula II are where $R_1$ is benzyl mono- or disubstituted on the ring portion with ($C_1$–$C_6$)alkyl, halogen, nitro, trifluoromethyl, trifluoromethoxy, cyano, hydroxy, ($C_1$–$C_6$)alkyl, hydroxy($C_1$–$C_6$)alkyl, amino, mono- or di($C_1$–$C_6$) alkylamino, aminomethyl, mono- or di($C_1$–$C_6$) alkylamino($C_1$–$C_6$)alkyl, or mono- or di($C_1$–$C_6$) alkylamino($C_1$–$C_6$)alkoxy; or $OR_7$, $O(CH_2)_nC(O)R_7$, $O(CH_2)_nNR_7R_8$, $O(CH_2)_nCO_2R_7$, $NR_7COR_8$, $COR_7$, $CONR_7R_8$ or $CO_2R_7$ where n=1, 2, 3, or 4; and $R_7$ and $R_8$ are the same or different and represent hydrogen, $SO_2Me$, or ($C_1$–$C_6$)alkyl; or $R_7$ and $R_8$ together with the nitrogen to which they are attached form a 5, 6 or 7 membered carbocyclic ring where up to two of the members are optionally hetero atoms selected from oxygen, sulfur and nitrogen, and where each member is optionally substituted with ($C_1$–$C_6$)alkyl;

except that $R_1$ is not 3-fluorobenzyl.

Even more preferred compounds of Formula II are those where $R_4$ is chloro and $R_a$ and $R_b$ are independently $C_1$–$C_6$ alkoxy, most preferably $C_1$–$C_3$ alkoxy. Particularly preferred compounds of Formula II are those where $R_3$ is butyl or isoamyl, i.e, 3-methylbutyl, $R_4$ is chloro, and $R_a$ and $R_b$ are independently $C_1$–$C_2$ alkoxy, most preferably methoxy.

In addition, the present invention encompasses compounds of the Formula III.

III wherein $R_1$ is as defined above for Formula I; and $R_3$ is $C_3$ or $C_6$ alkyl, preferably n-butyl, isoamyl, or n-pentyl;

$R_4$ is chloro or fluoro; and $R_a$ and $R_b$ independently represent hydrogen or $C_1$–$C_6$ alkoxy.

More preferred compounds of Formula II are where $R_1$ is benzyl mono- or disubstituted on the ring portion with ($C_1$–$C_6$)alkyl, halogen, nitro, trifluoromethyl, trifluoromethoxy, cyano, hydroxy, ($C_1$–$C_6$)alkyl, hydroxy($C_1$–$C_6$)alkyl, amino, mono- or di($C_1$–$C_6$) alkylamino, aminomethyl, mono- or di($C_1$–$C_6$) alkylamino($C_1$–$C_6$)alkyl, or mono- or di($C_1$–$C_6$) alkylamino($C_1$–$C_6$)alkoxy; or $OR_7$, $O(CH_2)_nC(O)R_7$, $O(CH_2)_nNR_7R_8$, $O(CH_2)_nCO_2R_7$, $NR_7COR_8$, $COR_7$, $CONR_7R_8$ or $CO_2R_7$ where n=1, 2, 3, or 4; and $R_7$ and $R_8$ are the same or different and represent hydrogen, $SO_2Me$, or ($C_1$–$C_6$)alkyl; or $R_7$ and $R_8$ together with the nitrogen to which they are attached form a 5, 6 or 7 membered carbocyclic ring where up to two of the members are optionally hetero atoms selected from oxygen, sulfur and nitrogen, and where each member is optionally substituted with ($C_1$–$C_6$)alkyl;

except that $R_1$ is not 3-fluorobenzyl.

Even more preferred compounds of Formula III are those where $R_4$ is chloro and $R_a$ and $R_b$ are independently $C_1$–$C_6$ alkoxy, most preferably $C_1$–$C_3$ alkoxy. Particularly preferred compounds of Formula III are those where $R_3$ is butyl or isoamyl, i.e, 3-methylbutyl, $R_4$ is chloro, and $R_a$ and $R_b$ are methoxy.

Particularly preferred $R_1$ groups in Formulae II and III are benzyl substituted in the 2- or 3-positions of its phenyl ring with hydroxy, $C_1$–$C_2$ alkyl, $C_1$–$C_2$ alkoxy, ω-[4-(($C_1$–$C_6$) alkyl)piperazinyl] ($C_1$–$C_4$)alkoxy, methyl sulfonate, 3-halopropoxy, carboxymethoxy, 2-, 3-, or 4-pyridyl($C_1$–$C_6$) alkyl, preferably 2-, 3-, or 4-pyridyl($C_1$–$C_2$)alkyl, 3-pyrrolidinyl($C_1$–$C_6$)alkoxy; tetrazolyl, halogen, preferably bromo, fluoro or chloro, alkylamino($C_1$–$C_6$)alkoxy, preferably 3-(methylamino)propoxy or 2-(ethylamino) ethoxy, morpholinyl($C_1$–$C_6$) alkoxy, preferably 3-morpholin-4-ylpropoxy or 2-(morpholin-4-yl)ethoxy, ω-piperidyl($C_1$–$C_4$)alkoxy, ($C_1$–$C_3$) alkoxycarbonylmethoxy, trifluoromethyl, (N-(methylsulfonyl) carbamoyl)methoxy, and nitro.

The most preferred among these 2- or 3-substituted benzyl groups are those substituted in the 2-position of the phenyl. ring.

Other particularly preferred $R_1$ groups of the invention are 2-fluoro-, 2-bromo- or 2-chloro-5-nitrobenzyl, 3,5-dihalobenzyl where the halogen is chloro or fluoro, 5-hydroxy($C_1$–$C_2$)alkyl-2-($C_1$–$C_3$)alkoxybenzyl, 5-($C_2$–$C_4$) alkanoyl-2-($C_1$–$C_3$)alkoxybenzyl, and 3-amino-5- or 6-($C_1$–$C_2$)alkoxybenzyl.

Still other preferred $R_1$ groups include alkenyl groups such as allyl or 1-buten-2- or 3-yl.

Other particularly preferred $R_1$ groups include 2- or 3-pyridyl.

By ω-substitution as used herein is meant the terminal position on, for example, an alkyl chain. Examples of such groups are 3-hydroxypropyl, 5-morpholin-4-ylpentyl, 3-piperazinylpropoxy, and 4-methoxybutyl.

By "alkyl", "lower alkyl", and "($C_1$–$C_6$)alkyl" in the present invention is meant straight or branched chain alkyl groups having 1–6 carbon atoms, such as, methyl, ethyl, propyl, isopropyl, n-butyl, sec-butyl, tert-butyl, pentyl, 2-pentyl, isopentyl, neopentyl, hexyl, 2-hexyl, 3-hexyl, and 3-methylpentyl.

By "alkoxy", "lower alkoxy", and "($C_1$–$C_6$)alkoxy" in the present invention is meant straight or branched chain alkoxy groups having 1–6 carbon atoms, such as, for example, methoxy, ethoxy, propoxy, isopropoxy, n-butoxy, sec-butoxy, tert-butoxy, pentoxy, 2-pentoxy, isopentoxy, neopentoxy, hexoxy, 2-hexoxy, 3-hexoxy, and 3-methylpentoxy.

By the term "halogen" in the present invention is meant fluorine, bromine, chlorine, and iodine.

By the term "patient" is meant human patients as well as domestic companion animals (pets) and livestock animals.

By "heteroaryl" is meant one or more aromatic ring systems of 5-, 6-, or 7-membered rings containing at least one and up to four heteroatoms selected from nitrogen, oxygen, or sulfur. Such heteroaryl groups include, for example, thienyl, furanyl, thiazolyl, imidazolyl, (is) oxazolyl, pyridyl, pyrimidinyl, (iso)quinolinyl, napthyridinyl, benzimidazolyl, benzoxazolyl. Preferred heteroaryls are thiazolyl and pyridyl.

By "aryl" is meant an aromatic carbocyclic group having a single ring (e.g., phenyl), multiple rings (e.g., biphenyl), or multiple condensed rings in which at least one is aromatic, (e.g., 1,2,3,4-tetrahydronaphthyl, naphthyl, anthryl, or phenanthryl), which is optionally mono-, di-, or trisubstituted with, e.g., halogen, lower alkyl, lower alkoxy, lower alkylthio, trifluoromethyl, lower acyloxy, aryl, heteroaryl, and hydroxy. A preferred aryl is phenyl.

Preferred $(C_1-C_6)$alkylamino groups are methylamino and ethylamino; preferred di$(C_1-C_6)$alkylamino groups are diethylamino and dimethylamino; preferred amino$(C_1-C_6)$alkyl groups are aminomethyl and 2-aminoethyl; preferred mono- and di$(C_1-C_6)$alkylamino$(C_1-C_6)$alkyl groups are methylaminomethyl, dimethylaminomethyl, ethylaminomethyl; and 2-(ethylamino)ethyl.

Representative compounds of the invention are shown below in Table 1.

TABLE 1

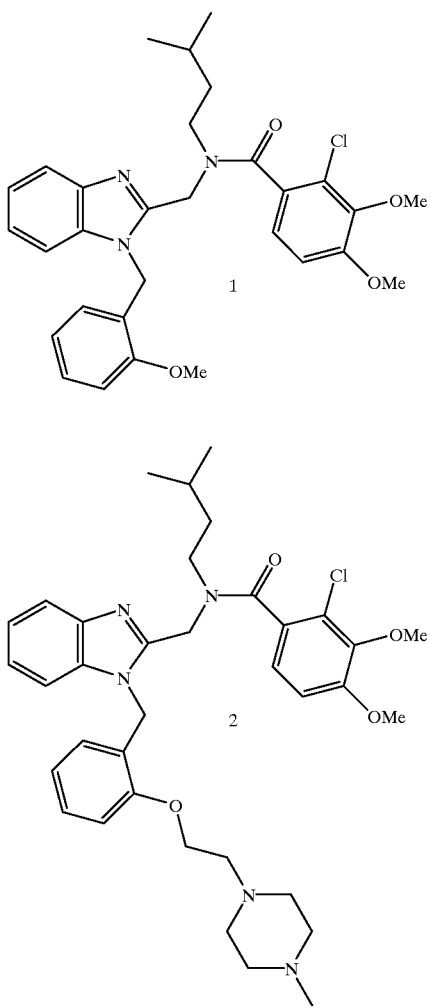

TABLE 1-continued

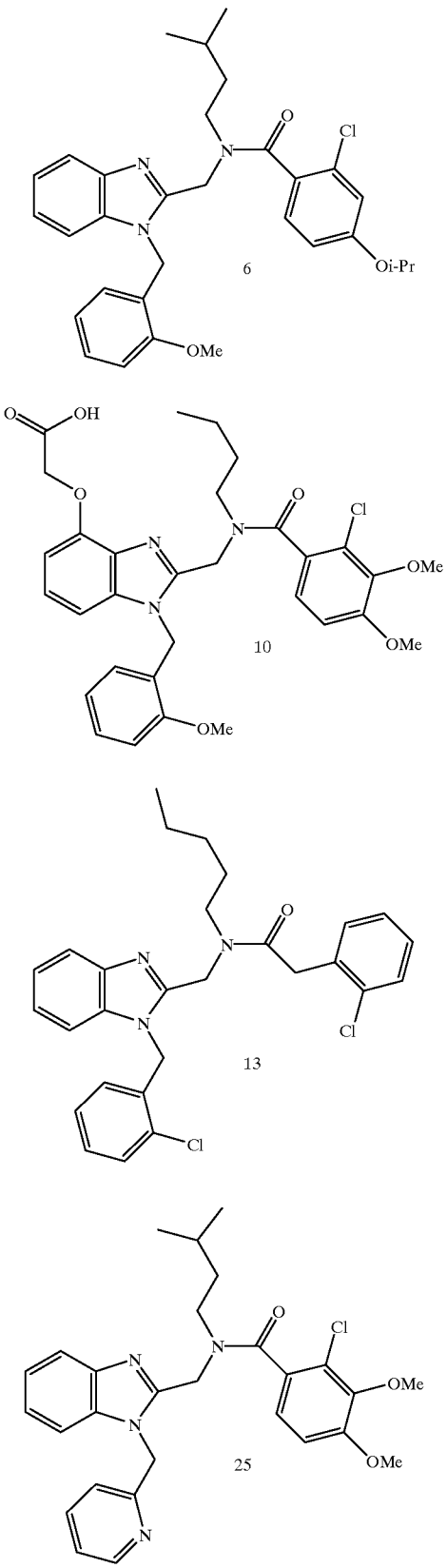

TABLE 1-continued

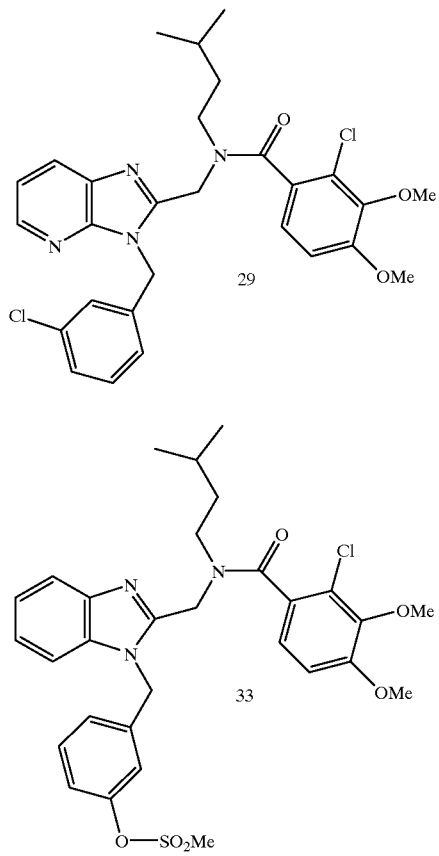

In certain situations, the compounds of Formula I may contain one or more asymmetric carbon atoms, so that the compounds can exist in different stereoisomeric forms. These compounds can be, for example, racemates or optically active forms. In these situations, the single enantiomers, i.e., optically active forms, can be obtained by asymmetric synthesis or by resolution of the racemates. Resolution of the racemates can be accomplished, for example, by conventional methods such as crystallization in the presence of a resolving agent, or chromatography, using, for example a chiral HPLC column.

Representative compounds of the present invention, which are encompassed by Formula I, include, but are not limited to the compounds described in the Examples and their pharmaceutically acceptable acid addition salts. In addition, if the compound of the invention is obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds.

Non-toxic pharmaceutical salts include salts of acids such as hydrochloric, phosphoric, hydrobromic, sulfuric, sulfinic, formic, toluenesulfonic, methanesulfonic, nitric, benzoic, citric, tartaric, maleic, hydroiodic, alkanoic such as acetic, HOOC—$(CH_2)n$—COOH where n is 0–4, and the like. Those skilled in the art will recognize a wide variety of non-toxic pharmaceutically acceptable addition salts.

The present invention also encompasses the acylated prodrugs of the compounds of Formula I. Those skilled in the art will recognize various synthetic methodologies which may be employed to prepare non-toxic pharmaceutically acceptable addition salts and acylated prodrugs of the compounds encompassed by Formula I.

Selective agonists or antagonists of the bradykinin $B_2$ receptor provide compounds useful in treatment of renal diseases, heart failure, hypertension, Meniere's disease, vaginal inflammation and pain, peripheral circulatory disorders, climacteric disturbance, retinochoroidal circulatroy disorders, myocardial ischemia, myocardial infarction, postmyocardial infarction syndrome, angina pectoris, restenosis after percutaneous transluminal coronary angioplasty, hepatitis, liver cirrhosis, pancreatitis, ileus, diabetes, diabetic complications, male infertility or glaucoma, or for the increase of permeability of blood-brain barrier, pain, asthma, rhinitis. The invention provides methods of treating patients suffering from such disorders with an amount of a compound of the invention sufficient to reduce the symptoms of the disorder.

Bradykinin has been shown to increase the permeability of blood-brain barrier and blood-brain tumor barrier. The invention provides a method of increasing the brain concentration of a CNS active compound which comprises administering to a patient in need of such treatment a compound of the invention, that is a selective agonist of the BK-2 receptor, along with a CNS active compound, and thereby increasing the brain concentration of the CNS active compound. In a particularly preferred embodiment the invention provides a method of increasing the brain concentration of anti-cancer and anti-tumor agents which comprises administering a patient suffering from brain cancer or a brain tumor a compound of the invention that is a selective agonist of the BK-2 receptor, along with an anti-cancer and anti-tumor agent, and thereby increasing the brain concentration of the anti-cancer or anti-tumor agent.

The compounds of general Formula I may be administered orally, topically, parenterally, by inhalation or spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition, there is provided a pharmaceutical formulation comprising a compound of general Formula I and a pharmaceutically acceptable carrier. One or more compounds of general Formula I may be present in association with one or more non-toxic pharmaceutically acceptable carriers and/or diluents and/or adjuvants and if desired other active ingredients. The pharmaceutical compositions containing compounds of general Formula I may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate;

granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensation products of the said partial esters with ethylene oxide, for example polyoxyethylene sorbitan monoleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono-or diglycerides. In addition, fatty acids such as oleic acid find use in the preparation of injectables.

The compounds of general Formula I may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

Compounds of general Formula I may be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

Dosage levels of the order of from about 0.1 mg to about 140 mg per kilogram of body weight per day are useful in the treatment of the above-indicated conditions (about 0.5 mg to about 7 g per patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient.

Frequency of dosage may also vary depending on the compound used and the particular disease treated. However, for treatment of most disorders, a dosage regimen of 4 times daily or less is preferred. For the treatment of chronic conditions, a dosage regimen of 1 or 2 times daily is particularly preferred. For the treatment of acute disorders, a single dose that rapidly reaches effective concentrations is desirable.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

Preferred compounds of the invention will have certain pharmacological properties. Such properties include, but are not limited to oral bioavailability, low toxicity, low serum protein binding and desirable in vitro and in vivo half-lifes. Penetration of the blood brain barrier for compounds used to treat CNS disorders is necessary, while low brain levels of compounds used to treat periphereal disorders are often preferred.

Assays may be used to predict these desirable pharmacological properties. Assays used to predict bioavailability include transport across human intestinal cell monolayers, including Caco-2 cell monolayers. Toxicity to cultured hepatocyctes may be used to predict compound toxicity. Penetration of the blood brain barrier of a compound in humans may be predicted from the brain levels of the compound in laboratory animals given the compound intravenously.

Serum protein binding may be predicted from albumin binding assays. Such assays are described in a review by Oravcová, et al. (Journal of Chromatography B (1996) volume 677, pages 1–27).

Compound half-life is inversely proportional to the frequency of dosage of a compound. In vitro half-lifes of compounds may be predicted from assays of microsomal half-life as described by Kuhnz and Gieschen (Drug Metabolism and Disposition, (1998) volume 26, pages 1120–1127).

The present invention also pertains to packaged pharmaceutical compositions for treating disorders responsive to BK-2 receptor modulation, e.g., treatment asthma, pain or rhinitis by BK-2 receptor modulation. The packaged pharmaceutical compositions include a container holding a therapeutically effective amount of at least one BK-2 receptor modulator as described supra and instructions for using the treating disorder responsive to BK-2 receptor modulation in the patient.

The present invention also pertains to methods of inhibiting the binding of bradykinin to the BK-2 receptor which methods involve contacting a compound of the invention with cells expressing BK-2 receptors, wherein the compound is present at a concentration sufficient to inhibit bradykinin binding to cells expressing a cloned human Bradykinin receptor in vitro and to methods for altering the signal-tranducing activity of BK-2 receptors, said method comprising exposing cells expressing such receptor to an effective amount of a compound of the invention.

The invention furthermore provides methods of using compounds of this invention as positive controls in assays for receptor activity and using appropriately labeled compounds of the invention as probes for the localization of receptors, particularly BK-2 receptors, in tissue sections. Such probes are useful for in vitro studies, such as binding assays and autoradiography of tissue sections and for in vivo techniques such as PET and SPECT scans.

Compounds of the invention can be prepared using the reactions depicted in Schemes I to VII. In Schemes I–VII, the groups $R_1$, $R_3$, $R_7$, $R_8$ and X are as defined in general Formula I. The numbers appearing below or adjacent the chemical structures in these schemes refer to intermediates and are not to be confused with the compound numbers found in the examples.

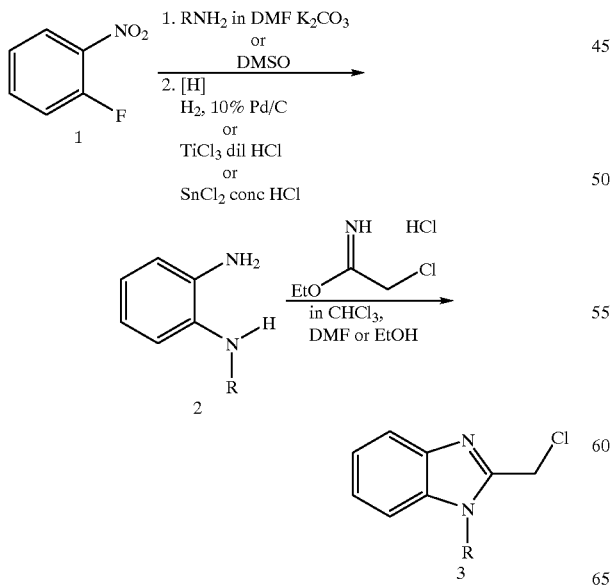

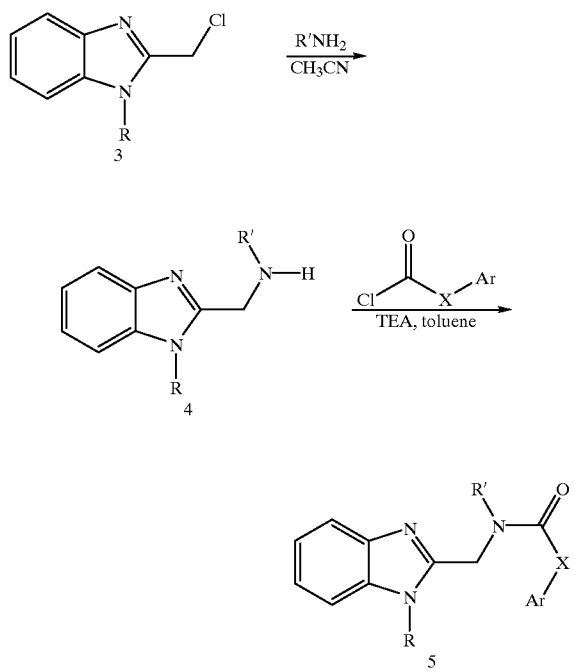

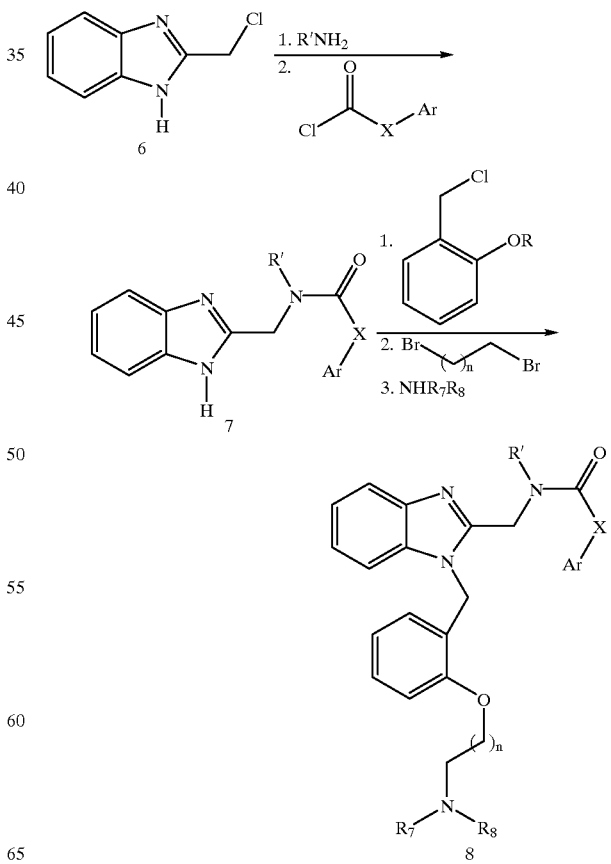

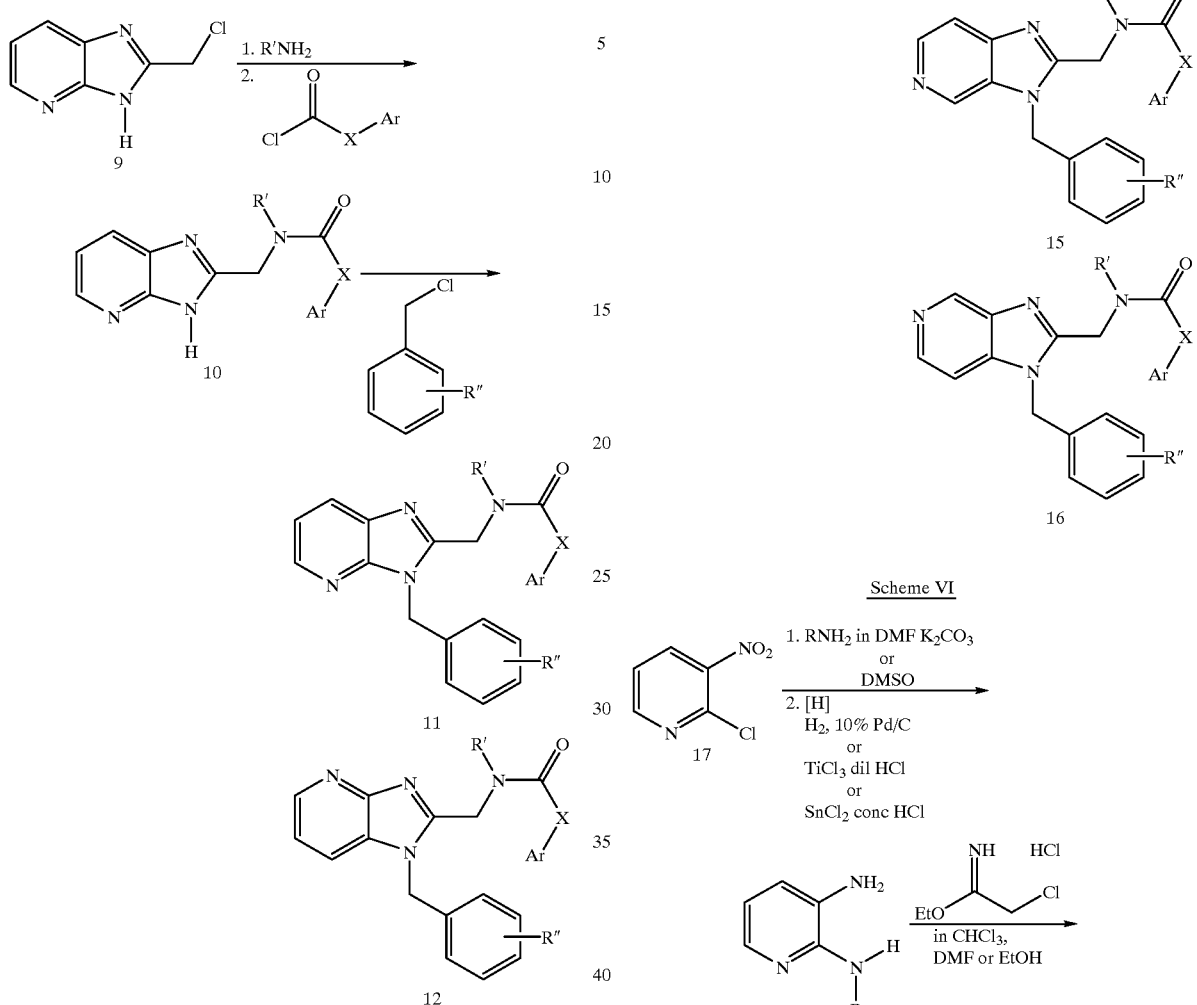
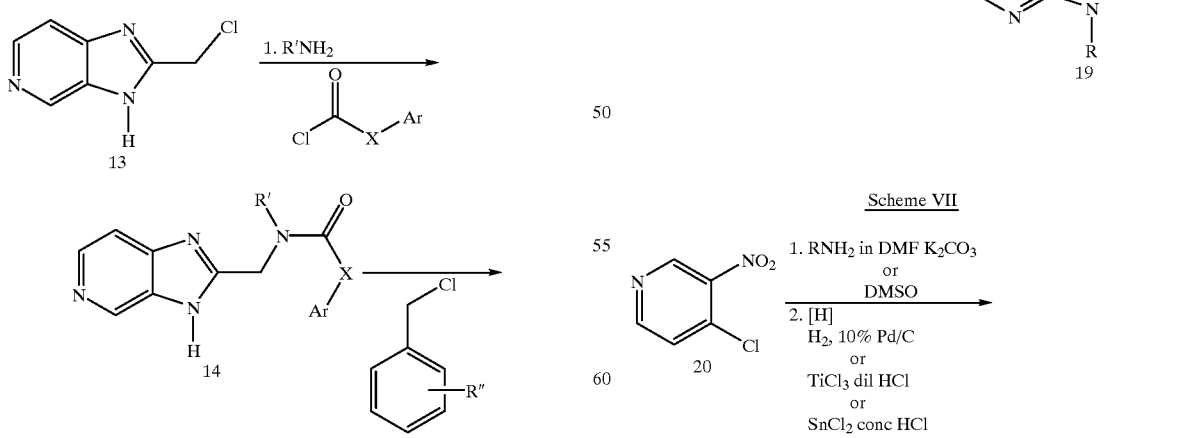

-continued

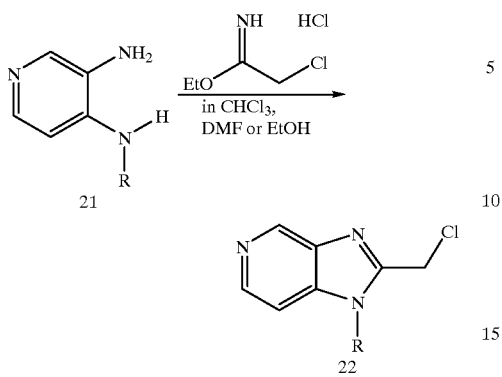

Those having skill in the art will recognize that the starting materials may be varied and additional steps employed to produce compounds encompassed by the present invention, as demonstrated by the following examples.

The disclosures of all articles and references mentioned in this application, including patents, are incorporated herein by reference.

The invention is illustrated further by the following examples which are not to be construed as limiting the invention in scope or spirit to the specific procedures described in them.

The starting materials and various intermediates may be obtained from commercial sources, prepared from commercially available organic compounds, or prepared using well known synthetic methods.

Representative examples of methods for preparing intermediates of the invention are set forth below.

EXAMPLE 1

General Procedure for the Preparation of Chloromethylbenzimidazoles as Outlined in Scheme I 1. Imidate hydrochloride:

A solution of 150 mL (2.37 mole) of chloroacetonitrile, 139 mL (2.37 mole) of ethanol in 1,200 mL of dry benzene is cooled to 0° C. in an ice/ethanol bath. Dry HCl gas is bubbled through the vigorously stirred solution for approximately 30 min. while the internal temperature is maintained below 10° C. The solution is allowed to stand at room temperature overnight. The resulting solid is filtered and washed with 2L of dry ether and allowed to air dry to afford 328 g (88%) of imidate hydrochloride.

2. 1-{[2-(chloromethyl)benzimidazolyl]methyl}-2-methoxybenzene:

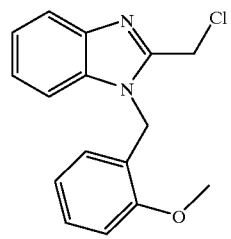

A solution of 31 g (0.14 mole) of (2-aminophenyl) [(2-methoxyphenyl)methyl]amine in 200 mL of anhydrous $CHCl_3$ is treated with 44 g (0.28 mole) of imidate at room temperature. The heterogeneous reaction mixture is allowed to stir for 1 hour at room temperature at which time no starting material is detectable by TLC. 100 mL of saturated $NaHCO_3$ is added and extracted 3×100 mL of $CH_2Cl_2$. The extracts are dried over anhydrous $Na_2SO_4$, the solvent removed in vacuo, and the residue chromatgraphed ($SiO_2$) with 50% ethyl acetate/hexane to afford 20 g (50%) of 1-{[2-(chloromethyl)benzimidazolyl]-methyl}-2-methoxybenzene. Mass Spec $M^+$ 287.

EXAMPLE 2

General Procedure for the Preparation of Benzimidazoles as Shown in Scheme II (2-Chloro-3,4-dimethoxyphenyl)-N-({1-[(2-methoxyphenyl)methyl]benzimidazol-2-yl}methyl)-N-(3-methylbutyl)carboxamide Compound 1

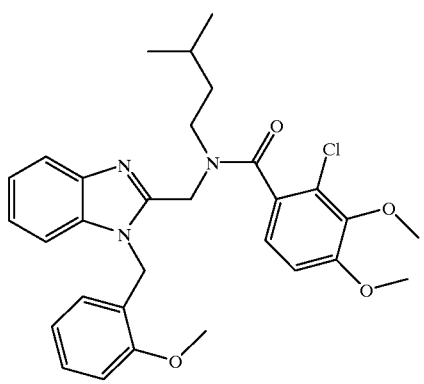

A solution of 5.4 mmole 1-{[2-(chloromethyl)-benzimidazolyl]methyl}-2-methoxybenzene in 20 mL of dryacetonitrile is treated with 10 mL of isoamylamine for 16 hours at room temperature. The solvent is removed in vacuo and the residue is partitioned between 30 mL of ethyl acetate and 10 mL of 1 N NaOH. The ethyl acetate layer is dried over anhydrous Na$_2$SO$_4$ and solvent removed in vacuo to afford 1.7 g 97% ({1-[(2-methoxyphenyl)methyl]benzimidazol-2-yl}methyl)(3-methylbutyl) amine. 2-Chloro-3,4-dimethoxybenzoylchloride (1.5 equ.) is treated with 1.0 equivalent of ({1-[(2-methoxyphenyl)methyl]benzimidazol-2-yl}methyl)(3-methylbutyl) amine in dichloromethane at room temperature for 1 hour. The reaction is quenched with 1 N NaOH and partitioned between dichloromethane and water. The organic layer is dried with Na$_2$SO$_4$ and the solvent removed in vacuo. The residue is chromatographed (SiO$_2$) with ethyl acetate to afford 95% of (2-chloro-3,4-dimethoxyphenyl)-N-({1-[(2-methoxyphenyl)methyl]benzimidazol-2-yl}methyl)-N-(3-methylbutyl)carboxamide (Compound 1). Mass Spec M$^+$ 537.

EXAMPLE 3

General Procedure for the Preparation of Benzimidazoles as Shown in Scheme 3

(2-Chloro-3,4-dimethoxyphenyl)-N-(3-methylbutyl)-N-{[1-({2-[3-(4-methylpiperazinyl)propoxy]phenyl}methyl)-benzimidazol-2-yl]methyl}carboxamide

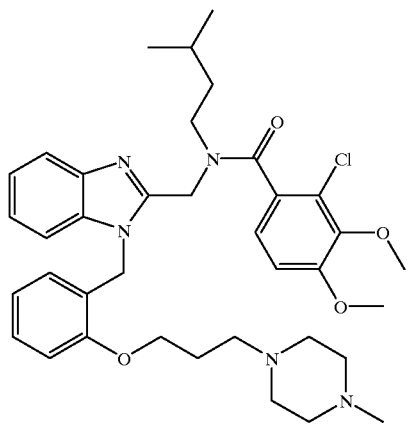

A solution of 5.0 9 (30.0 mmole) of 2-(chloromethyl)benzimidazole in 25 mL of anhydrous 1-methyl-2-pyrrolidinone is treated at 0° C. with 17.4 mL (150 mmole) of isoamylamine. The reaction mixture is allowed to warm to room temperature and stir for 16 hr. The reaction mixture is poured into 800 mL of ice/water, and the tan solid filtered and dried to afford 6.08 g (93%) of (benzimidazol-2-ylmethyl)(3-methylbutyl)amine.

A solution of 3.0 g (13.8 mmole) of (benzimidazol-2-ylmethyl) (3-methylbutyl)amine in 150 mL of 1:1:1 ethyl acetate, acetone, water is treated with 3.66 g (34.5 mmole) Na$_2$CO$_3$ and a solution of 3.22 g (13.7 mmole) of 2-chloro-3,4-dimethoxybenzoyl chloride in 50 mL of acetone at 0° C. The resulting mixture is allowed to warm to room temperature for 1 hour. The reaction solution is diluted with 300 mL of ethyl acetate and then washed with 2×60 mL water, 1×60 mL sat. NaHCO$_3$, and 1×60 mL of brine. The resulting organic layer is dried over anhydrous Na$_2$SO$_4$ and the solvent removed in vacuo. The residue is treated with 150 mL of methanol and 1.1 g of NaOH at reflux for 2 hours and then allow to cool to room temperature for 2 hours. The resulting solution is evaporated under reduced pressure and partioned between ethyl acetate 200 mL and water 100 mL. The ethyl acetate extracts are dried over anhydrous Na$_2$SO$_4$ and the solvent removed in vacuo. The resulting residue is flash chromatographed (1:1 ethyl acetate/hexanes) to afford 2.82 g (49%) of N-(benzimidazol-2-ylmethyl)(2-chloro-3,4-dimethoxyphenyl)-N-(3-methylbutyl)carboxamide.

A solution of 1.0 g (2.4 mmole) of N-(benzimidazol-2-ylmethyl)(2-chloro-3,4-dimethoxyphenyl)-N-(3-methylbutyl)-carboxamide and 1.56 g (4.8 mmole) of Cs$_2$CO$_3$ in 5 mL anhydrous N,N-dimethylformamide is treated with 0.64 g (2.88 mmole) of 2-(chloromethyl)phenyl methylsulfonate at room temperature and heated to 50° C. for 1 hr. The reaction is cooled to room temperature, diluted with 60 mL of ethyl acetate and washed with 3×20 mL water and 1×20 mL brine, dried over anhydrous Na$_2$SO$_4$ and the solvent is removed in vacuo. The resulting residue is flash chromatographed (2% MeOH/CH$_2$Cl$_2$/0.5% NH$_4$OH) to afford 1.26 g (88%) of 2-[(2-{[(2-chloro-3,4-dimethoxyphenyl)-N-(3-methylbutyl)carbonylamino]methyl}benzimidazolyl)methyl]-phenyl methylsulfonate.

A solution of 1.2 g (2.0 mmole) of 2-[(2-{[(2-chloro-3,4-dimethoxyphenyl)-N-(3-methylbutyl)-carbonylamino]-methyl}benzimidazolyl)methyl]-phenyl methylsulfonate and 0.321 g (8.0 mmole) of NaOH in methanol is warmed to 50° C. for 3.5 hours. The resulting mixture is cooled to room temperature, evaporated at reduced pressure, diluted with 100 mL of ethyl acetate, washed with 1×30 mL sat. NH$_4$Cl and 1×30 mL brine, dried over anhydrous Na$_2$SO$_4$ and the solvent is removed in vacuo. The resulting residue is flash chromatographed (3% MeOH/CH$_2$Cl$_2$/0.5% NH$_4$OH) to afford 0.864 g (83%) of (2-chloro-3,4-dimethoxyphenyl)-N-({1-[(2-hydroxyphenyl)methyl]benzimidazol-2-yl}methyl)-N-(3-methylbutyl) carboxamide.

A solution of 350 mg (0.67 mmole) of (2-chloro-3,4-dimethoxyphenyl)-N-({1-[(2-hydroxyphenyl)methyl]benzimidazol-2-yl}methyl)-N-(3-methylbutyl) carboxamide and 278 mg (2.01 mmole) of K$_2$CO$_3$ in 2 mL of anhydrous N,N-dimethylformamide is treated with 79.1 µL (0.737 mmole) 1-chloro-3-iodo propane at room temperature for 19 hr. The resulting solution is diluted with 60 mL of ethyl acetate, washed with 3×20 mL water and 1×20 mL of brine, dried over anhydrous Na$_2$SO$_4$ and the solvent is removed in vacuo to afford 400 mg (99%) of (2-chloro-3,4-dimethoxyphenyl)-N-[(1-{[2-(3-chloropropoxy)phenyl]methyl}benzimidazol-2-yl)methyl]-N-(3-methylbutyl) carboxamide.

A solution of 395 mg (0.66 mmole) of (2-chloro-3,4-dimethoxyphenyl)-N-[(1-{[2-(3-chloropropoxy)phenyl]methyl}benzimidazol-2-yl)methyl]-N-(3-methylbutyl) carboxamide in 6 mL of acetone is treated with 99 mg (3.30 mmole) of NaI at reflux for 16 hrs, at which time another 3.30 mmole of NaI is added and heated for an additional 24 hrs. The solution is evaporated under reduced pressure, the residue is diluted with 30 mL of ethyl acetate, washed with 2×10 mL water and 1×10 mL brine, dried over anhydrous Na$_2$SO$_4$ and the solvent is removed in vacuo. The residue is dissolved in anhydrous 1-methyl-2-pyrrolidinone at 100 mg/mL and 1 mL of the solution is treated with an excess of N-methyl piperazine at 50° C. for 16 hr. The resulting solution is cooled to room temperature, washed with 3×1 mL water and 1×1 mL brine, dried over anhydrous Na$_2$SO$_4$ and the solvent is removed in vacuo. The residue is prep-plate chromatographed (5% MeOH/CH$_2$Cl$_2$/0.5% NH$_4$OH) to afford 65 mg (70%) of 2-chloro-3,4-dimethoxyphenyl)-N-(3-methylbutyl)-N-{[1-({2-[3-(4-methylpiperazinyl)propoxy]phenyl}methyl)benzimidazol-2-yl]methyl}carboxamide. Mass Spec M$^+$ 663.

Following the above procedures, compounds 11, 12, 15 and 16 are prepared starting from 2-(chloromethyl)imidazolo[5,4-b]pyridine and 2-(chloromethyl)imidazolo[5,4-c]pyridine respectively. See also Cleve et al., *Justus Liebigs Ann. Chem.* 1971, 747, 158–171.

EXAMPLE 4

The following compounds are prepared essentially according to the procedures described in Examples 1–3, and as shown in Schemes I–VII:

(a) 2-{2-[(2-{[(2-chloro-3,4-dimethoxyphenyl)-N-(3-methylbutyl)carbonylamino]methyl}benzimidazolyl)methyl]phenoxy)acetic acid; Mass Spec. M$^+$ 581 amu.; (Compound 3).

(b) (2-chloro-3,4-dimethoxyphenyl)-N-(3-methylbutyl)-N-{[3-(2-pyridylmethyl)imidazolo[5,4-b]pyridin-2-yl]methyl}carboxamide; Mass Spec M$^+$ 509 amu.; (Compound 4).

(c) 2-(2-chlorophenyl)-N-({3-[(2-methoxyphenyl)methyl]imidazolo[5,4-b]pyridin-2-yl}methyl)-N-(3-methylbutyl)acetamide Mass Spec M$^+$ 492 amu.; (Compound 5).

(d) [2-chloro-4-(methylethoxy)phenyl]-N-({3-[(2-methoxyphenyl)methyl]imidazolo[5,4-b]pyridin-2-yl}methyl)-N-(3-methylbutyl)carboxamide; Mass Spec M$^+$ 536 amu.; (Compound 6).

(e) (2-chloro-3,4-dimethoxyphenyl)-N-((1-[(2-methoxyphenyl)methyl]imidazolo[4,5-c]pyridin-2-yl}methyl)-N-(3-methylbutyl)carboxamide; Mass Spec M$^+$ 538 amu.; (Compound 7).

(f) (2-chloro-3,4-dimethoxyphenyl)-N-(3-methylbutyl)-N-[(1-({[3-(3-pyrrolidinylpropoxy)phenyl]methyl}benzimidazol-2-yl)methyl]carboxamide; Mass Spec M$^+$ 634 amu.; (Compound 8).

(g) (2-chloro-3,4-dimethoxyphenyl)-N-(3-methylbutyl)-N-[(1-prop-2-enylbenzimidazol-2-yl)methyl]carboxamide; Mass Spec M$^+$ 57 amu.; (Compound 9).

(h) 2-(2-{[(2-chloro-3,4-dimethoxyphenyl)-N-(3-methylbutyl)carbonylamino]methyl}-1-[(2-methoxyphenyl)methyl]benzimidazol-4-yloxy)acetic acid; (Compound 10).

(i) 2-{2-[(2-{[(2-chloro-3,4-dimethoxyphenyl)-N-(3-methylbutyl)carbonylamino]methyl}benzimidazolyl)methyl]phenoxy-N-(methylsulfonyl) acetamide; (Compound 11).

(j) (2-chloro-3,4-dimethoxyphenyl)-N-(3-methylbutyl)-N-({1-[(2-(2H-1,2,3,4-tetrazol-5-yl)phenyl)methyl]benzimidazol-2-yl}methylcarboxamide; (Compound 12).

(k) 2-(2-chlorophenyl)-N-({1-[(2-chlorophenyl)methyl]benzimidazol-2-yl}methyl)-N-pentylacetamide; Mass Spec. M+495 amu.; (Compound 13).

(l) 2-(2-chlorophenyl)-N-({1-[(2-chlorophenyl)methyl]benzimidazol-2-yl}methyl)-N-(3-methylbutyl)acetamide; Mass Spec. M+495 amu.; (Compound 14).

(m) (2-chloro-3,4-dimethoxyphenyl)-N-({1-[(2-methoxy-5-nitrophenyl)methyl]benzimidazol-2-yl}methyl)-N-(3-methylbutyl)carboxamide; Mass Spec. M+583 amu.; (Compound 15).

(n) (2-chloro-3,4-dimethoxyphenyl)-N-({1-[(2-methoxyphenyl)methyl]benzimidazol-2-yl}methyl)-N-pentylcarboxamide; Mass Spec. M$^+$ 537 amu.; (Compound 16).

(o) N-({3-[(3,5-dichlorophenyl)methyl]imidazolo[5,4-b]pyridin-2-yl}methyl)(2-chloro-3,4-dimethoxyphenyl)-N-(3-methylbutyl)carboxamide; Mass Spec. M$^+$ 577 amu.; (Compound 17).

(p) (2-chloro-3,4-dimethoxyphenyl)-N-({1-[(2-hydroxyphenyl)methyl]benzimidazol-2-yl)methyl)-N-(3-methylbutyl)carboxamide; Mass Spec. M$^+$ 523 amu.; (Compound 18).

(q) 2-[(2-{[(2-chloro-3,4-dimethoxyphenyl)-N-(3-methylbutyl)carbonylamino]methyl}benzimidazolyl)methyl]phenyl methylsulfonate; Mass Spec. M$^+$ 601 amu.; (Compound 19).

(r) (2-chloro-3,4-dimethoxyphenyl)-N-[(1-{[5-(hydroxyethyl)-2-methoxyphenyl]methyl}benzimidazol-2-yl)methyl]-N-(3-methylbutyl) carboxamide; Mass Spec. M$^+$ 581 amu.; (Compound 20).

(s) N-({1-[(5-acetyl-2-methoxyphenyl)methyl]benzimidazol-2-yl}methyl)(2-chloro-3,4-dimethoxyphenyl)-N-(3-methylbutyl)carboxamide; Mass Spec. M$^+$ 579 amu.; (Compound 21).

(t) (2-chloro-3,4-dimethoxyphenyl)-N-({1-[(2-chlorophenyl)methyl]benzimidazol-2-yl}methyl)-N-(3-methylbutyl)carboxamide; Mass Spec. M$^+$ 541 amu.; (Compound 22).

(u) (2-chloro-3,4-dimethoxyphenyl)-N-{[1-({3-[3-(methylamino)propoxy]phenyl}methyl)benzimidazol-2-yl]methyl}-N-(3-methylbutyl)carboxamide; Mass Spec. M$^+$ 594 amu.; (Compound 23).

(v) (2-chloro-3,4-dimethoxyphenyl)-N-(3-methylbutyl)-N-{[1-({3-[3-(4-methylpiperazinyl)propoxy]phenyl}methyl) benzimidazol-2-yl]methyl}carboxamide; Mass Spec. M$^+$ 663 amu.; (Compound 24).

(w) (2-chloro-3,4-dimethoxyphenyl)-N-(3-methylbutyl)-N-{[1-(2-pyridylmethyl)benzimidazol-2-yl]methyl}carboxamide; Mass Spec. M$^+$ 508 amu.; (Compound 25).

(x) (2-chloro-3,4-dimethoxyphenyl)-N-{[1-({3-[2-(ethylamino)ethoxy]phenyl}methyl)benzimidazol-2-yl]methyl}-N-(3-methylbutyl)carboxamide; Mass Spec. M$^+$ 594 amu.; (Compound 26).

(y) (2-chloro-3,4-dimethoxyphenyl)-N-({1-[(2-fluorophenyl)methyl]benzimidazol-2-yl}methyl)-N-(3-methylbutyl)carboxamide; Mass Spec. M$^+$ 525 amu.; (Compound 27).

(z) N-butyl(2-chloro-3,4-dimethoxyphenyl)-N-({1-[(2-methoxyphenyl)methyl]benzimidazol-2-yl}methyl)carboxamide; Mass Spec. M$^+$ 523 amu.; (Compound 28).

(aa) (2-chloro-3,4-dimethoxyphenyl)-N-({3-[(3-chlorophenyl)methyl]imidazolo[5,4-b]pyridin-2-yl}methyl)-N-(3-methylbutyl)carboxamide; Mass Spec. M$^+$ 542 amu.; (Compound 29).

(bb) (2-chloro-3,4-dimethoxyphenyl)-N-(3-methylbutyl)-N-({1-[(2-methylphenyl)methyl]benzimidazol-2-yl}methyl)carboxamide; Mass Spec. M+ 521 amu.; (Compound 30).

(cc) (2-chloro-3,4-dimethoxyphenyl)-N-(3-methylbutyl)-N-[(1-{[3-(3-morpholin-4-ylpropoxy)phenyl]methyl}benzimidazol-2-yl)methyl]carboxamide; Mass Spec. M+ 650 amu.; (Compound 31).

(dd) (2-chloro-3,4-dimethoxyphenyl)-N-(3-methylbutyl)-N-{[1-({3-[2-(4-methylpiperazinyl)ethoxy]phenyl}methyl)-benzimidazol-2-yl]methyl}carboxamide; Mass Spec. M+ 649 amu.; (Compound 32).

(ee) 3-[(2-{[(2-chloro-3,4-dimethoxyphenyl)-N-(3-methylbutyl)carbonylamino]methyl}benzimidazolyl)methyl]phenyl methylsulfonate; Mass Spec. M+ 601 amu.; (Compound 33).

(ff) (2-chloro-3,4-dimethoxyphenyl)-N-(3-methylbutyl)-N-[(1-{[3-(2-piperidylethoxy)phenyl]methyl}benzimidazol-2-yl)methyl]carboxamide; Mass Spec. M+ 634 amu.; (Compound 34).

(gg) (2-chloro-3,4-dimethoxyphenyl)-N-({1-[(3-hydroxyphenyl)methyl]benzimidazol-2-yl}methyl)-N-(3-methylbutyl)carboxamide; Mass Spec. M+ 523 amu.; (Compound 35).

(hh) ethyl 2-{2-[(2-{[(2-chloro-3,4-dimethoxyphenyl)-N-(3-methylbutyl)carbonylamino]methyl}benzimidazolyl)methyl]-phenoxy}acetate; Mass spec. M+ 609 amu.; (Compound 36).

(ii) (2-chloro-3,4-dimethoxyphenyl)-N-({3-[2-methoxyphenyl)methyl]imidazolo[5,4-b]pyridin-2-yl}methyl)-N-(3-methylbutyl)carboxamide; Mass Spec. M+ 538 amu.; (Compound 37).

(jj) N-({1-[(3-amino-6-methoxyphenyl)methyl]benzimidazol-2-yl}methyl)(2-chloro-3,4-dimethoxyphenyl)-N-(3-methylbutyl)carboxamide; Mass Spec. M+ 552 amu.; (Compound 38).

(kk) (2-chloro-3,4-dimethoxyphenyl)-N-(3-methylbutyl)-N-{[1-({2-[2-(4-methylpiperazinyl)ethoxy]phenyl}methyl)-benzimidazol-2-yl]methyl}carboxamide; Mass Spec. M+ 649 amu.; (Compound 39).

(ll) N-butyl(2-chloro-3,4-dimethoxyphenyl)-N-({1-[(3-fluorophenyl)methyl]benzimidazol-2-yl}methyl)carboxamide; Mass Spec. M+ 511 amu.; (Compound 40).

(mm) (2-chloro-3,4-dimethoxyphenyl)-N-(3-methylbutyl)-N-[(1-{[2-(trifluoromethyl)phenyl]methyl}benzimidazol-2-yl)methyl]carboxamide; Mass Spec. M+ 575 amu.; (Compound 41).

(nn) [2-chloro-4-(methylethoxy)phenyl]-N-(3-methylbutyl)-N-({1-[(2-nitrophenyl)methyl]benzimidazol-2-yl}methylcarboxamide; Mass Spec. M+ 550 amu.; (Compound 42).

(oo) (2-chloro-3,4-dimethoxyphenyl)-N-[(4-methoxy-1-prop-2-enylbenzimidazol-2-yl)methyl]-N-(3-methylbutyl)carboxamide; Mass Spec. M+ 487 amu.; (Compound 43).

EXAMPLE 5

Ligand Binding Assay on Sf9 Cell Membranes Expressing the BK-2 Receptor

This assay is a standard assay of BK-2 receptor binding, and is used to determine the high affinity of compounds of this invention for the BK-2 (bradykinin $B_2$) receptor.

Binding Buffer: 50 mM Tris, pH 7.0 (4° C.), 0.14 grams per liter bacitracin (approx. 50,000 units of activity/liter, lot# 103746 from Amersham), and $10_{-6}$ M captopril. Captopril is purchased from Sigma C-4042, 2.17 mg in 10 ml of milli-Q water produces a $10_{-3}$ M stock. Stock can be stored for 3 weeks in the refrigerator. 1.0 ml of stock per liter buffer =$10_{-6}$ M final concentration.

Ligand Preparation: 0.25 nM $^3$H-Bradykinin is used. 10 µl of stock +100 ml of binding buffer gives approximately 600 cpm/5 ul aliquot.

Non-Specific Preparation: NS binding is defined by unlabeled bradykinin at 1 µM final concentration. Aliquots are stored at –20° C. in 0.5% BSA at a concentration of $10_{-3}$ M. Aliquots are then diluted 1:100 for an intermediate concentration of $10_{-5}$ M.

Baculovirus-infected Sf9 cells expressing recombinant human bradykinin $B_2$ receptors are harvested 48 hours post infection via centrifugation at 3000×g. Cells are washed with ice-cold PBS and stored at –70° C. until needed. Frozen cell pellets are resuspended in ice cold Washing Buffer (50mM Tris pH 7.0) and homogenized via POLYTRON for 30 seconds at setting 5. Membranes are centrifuged at 40,000×g for 10 min. Pellets are resuspended in Washing Buffer with the aid of a polytron and centrifuged again. Membranes are resuspended in binding buffer at a concentration of 133 µg/ml. This corresponds to 20 µg of protein per 150 µl.

When measuring non-specific binding, incubations contain 150 µl of Sf9 cell membranes prepared as described above, 50 µl $^3$H-Bradykinin (0.25 nM), 25 µl unlabeled bradykinin at 1 µM final concentration and 2 µl DMSO. Incubations for determining test compound binding contain 175 µl of Sf9 cell membranes, 50 µl $^3$H-Bradykinin (0.25 nM), and test compound in 2 µl DMSO. The concentration of the test compound is generally 1 µM for displacement studies. The binding reaction components are incubated for 2 hrs at 4° C. in Falcon U bottom plates. Plates are harvested on the microbeta harvester onto 0.5% PEI pretreated unifilters. After harvesting, the filters are dried overnight. 17 µl of beta-scint is added to each well before the unifilters are counted in the microbeta counters. Data are collected in duplicate determinations, averaged and % inhibition of total specific binding is calculated. Total Specific Binding=Total–Nonspecific. In some cases, the amounts of unlabeled drug are varied and total displacement curves of binding are carried out. Data are converted to a form for the calculation of $IC_{50}$ and Hill Coefficient (nH). Ki's are subsequently determined by the Cheng-Prusoff equation (Cheng, Y. C.; Prusoff, W. C. *Biochem. Pharmacol.* 1972, 22, 3099–3108). In the described assay, compounds of the invention have Ki's of less than 1 uM, preferred compounds of the invention exhibit Ki values of less than 500 nM and more preferred compounds of the invention exhibit Ki values of less than 100 nM.

EXAMPLE 6

BK-2 Receptor Mediated Calcium Mobilization

The agonist and antagonist properties of the compounds of the invention can be evaluated by the following assay.

CHO cells stably expressing the BK-2 receptor are grown in Ham's F-12 media supplemented with 250 µg/ml G418, 1 µg/ml tetracycline, 7 µg/ml puromycin, 10% fetal bovine serum and 25 mM Hepes, pH=7.4. Forty-eight hours prior to assay, the cell growth media is replaced with another medium that does not contain the tetracycline. Twenty-four hours prior to experiment sodium butyrate is added to a final concentration of 10 mM. On the day of assay, cells, grown to 70–90% confluence in 96-well plates, are washed with Krebs-Ringer buffer (25 mM HEPES, 5 mM KCl, 0.96 mM $NaH_2PO_4$, 1 mM $MGSO_4$, 2 mM $CaCl_2$, 5 mM glucose, and 1 mM probenecid pH 7.4) and are then incubated for 1–2 hours in the above buffer supplemented with Fluo3-AM (2.5 ñ 10 (g/ml; Teflabs) at 37° C. in an environment containing 5% $CO_2$. The wells are then washed twice with Krebs-Ringers buffer. Agonist-induced (bradykinin) calcium mobilization is monitored using either Fluoroskan Ascent (Labsystems) or FLIPR (Molecular Devices) instruments. The agonists, either bradykinin or drug candidates, are added to the cells and fluorescence responses are continuously recorded for up to 5 min. For the examination of antagonist drug candidates, compounds, at a concentration of 1 uM in DMSO, are preincubated with the cells for up to 30 minutes prior to administration of the bradykinin agonist. Bradykinin agonist is generally applied at a concentration sufficient to induce 50% maximal activity. Responses are recorded for up to 5 min. Kaleidagraph software (Synergy Software, Reading, Pa.) is utilized to fit the data to the equation $y=a*(1/(1+(b/x)c))$ to determine the $EC_{50}$ value or $IC_{50}$ value for the response. In this equation, y is the maximum fluorescence signal, x is the concentration of the agonist or antagonist, a is the Emax, b corresponds to the $EC_{50}$ or $IC_{50}$ value, and, finally, c is the Hill coefficient.

EXAMPLE 7

Preparation of Radiolabeled Probe Compounds of the Invention

The compounds of the invention are prepared as radiolabeled probes by carrying out their synthesis using precursors comprising at least one atom that is a radioisotope. The radioisotope is preferably selected from of at least one of carbon (preferably $^{14}C$), hydrogen (preferably $^{3}H$), sulfur (preferably $^{35}S$), or iodine (preferably $^{125}I$). Such radiolabeled probes are conveniently synthesized by a radioisotope supplier specializing in custom synthesis of radiolabeled probe compounds. Such suppliers include Amersham Corporation, Arlington Heights, Ill.; Cambridge Isotope Laboratories, Inc. Andover, Mass.; SRI International, Menlo Park, Calif.; Wizard Laboratories, West Sacramento, Calif.; ChemSyn Laboratories, Lexena, Kans.; American Radiolabeled Chemicals, Inc., St. Louis, Mo.; and Moravek Biochemicals Inc., Brea, Calif.

Tritium labeled probe compounds are also conveniently prepared catalytically via platinum-catalyzed exchange in tritiated acetic acid, acid-catalyzed exchange in tritiated trifluoroacetic acid, or heterogeneous-catalyzed exchange with tritium gas. Such preparations are also conveniently carried out as a custom radiolabeling by any of the suppliers listed in the preceding paragraph using the compound of the invention as substrate. In addition, certain precursors may be subjected to tritium-halogen exchange with tritium gas, tritium gas reduction of unsaturated bonds, or reduction using sodium borotritide, as appropriate.

EXAMPLE 8

Use of Compounds of the Invention as Probes for BK-2 Receptors in Cultured Cells and Tissue Samples The presence of BK-2 receptors in cultured cells or tissue samples may be ascertained by the procedures described by Hall and Morton in the chapter entitled "Immunopharmacology of the Bradykinin Receptor" of *The Handbook of Immunopharmacology—The Kinin Systems* (1997) Academic Press, S. C. Farmer, editor, using radiolabeled compounds of the invention prepared as described in the preceding Example 7.

The invention and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the spirit or scope of the present invention as set forth in the claims. To particularly point out and distinctly claim the subject matter regarded as invention, the following claims conclude this specification.

What is claimed is:

1. A compound of the formula:

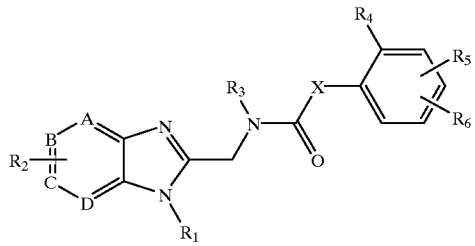

or pharmaceutically acceptable salts thereof wherein:

$R_1$ is not 3-fluorobenzyl and represents
  (i) $(C_2-C_6)$alkenyl; or
  (ii) $R_1$ represents aryl$(C_1-C_6)$alkyl or heteroaryl $(C_1-C_6)$alkyl, where the ring portion of each is optionally substituted with one, two or three groups independently selected from halogen, nitro, trifluoromethyl, trifluoromethoxy, cyano, hydroxy, $(C_1-C_6)$alkyl, hydroxy$(C_1-C_6)$alkyl, amino, mono- or di$(C_1-C_6)$alkylamino, amino$(C_1-C_6)$alkyl, mono- or di$(C_1-C_6)$alkylamino$(C_1-C_6)$alkyl, mono- or di$(C_1-C_6)$alkylamino$(C_1-C_6)$alkoxy, or
  (iii) $OR_7$, $O(CH_2)_nC(O)R_7$, $O(CH_2)_nNR_7R_8$, $O(CH_2)_nCO_2R_7$, $NR_7COR_8$, $COR_7$, $CONR_7R_8$ or $CO_2R_7$ where
    n=1, 2, 3, or 4 and
    $R_7$ and $R_8$ are the same or different and represent hydrogen, $SO_2Me$, or $(C_1-C_6)$alkyl; or
    $R_7$ and $R_8$ together with the nitrogen to which they are attached form a 5, 6 or 7 membered carbocyclic ring where up to two of the members in the ring are optionally hetero atoms selected from oxygen, sulfur and nitrogen, and where each member is optionally substituted with $(C_1-C_6)$alkyl;

$R_2$ represents
  hydrogen, hydroxy, halogen, trifluoromethyl, trifluoromethoxy, amino$(C_1-C_6)$alkyl, mono- or di$(C_1-C_6)$alkylamino$(C_1-C_6)$, or mono- or di$(C_1-C_6)$alkylamino$(C_1-C_6)$alkoxy; or
  $OR_7$, $O(CH_2)_nC(O)R_7$, $O(CH_2)_nNR_7R_8$, $O(CH_2)_nCO_2R_7$, $NR_7COR_8$, $COR_7$, $CONR_7R_8$ or $CO_2R_7$ where
    n=1, 2, 3, or 4; and
    $R_7$ and $R_8$ are the same or different and represent hydrogen, $SO_2Me$, or $(C_1-C_6)$alkyl; or
    $R_7$ and $R_8$ together with the nitrogen to which they are attached form a 5, 6 or 7 membered carbocyclic ring where up to two of the members are optionally hetero atoms selected from oxygen, sulfur and nitrogen, and where each member is optionally substituted with $(C_1-C_6)$alkyl;

$R_3$ represents $(C_1-C_6)$alkyl;

$R_4$ represents halogen or trifluoromethyl;

$R_5$ and $R_6$ are the same or different and represent hydrogen, trifluoromethyl, trifluoromethoxy, cyano, $(C_1-C_6)$alkyl, halogen, $(C_1-C_6)$alkylamino$(C_1-C_6)$ alkyl, mono or di$(C_1-C_6)$alkylamino$(C_1-C_6)$, or mono- or di$(C_1-C_6)$alkylamino$(C_1-C_6)$alkoxy; or $R_4$ and $R_5$ together with the carbon atoms to which they are attached form a 5 or 6 membered aromatic ring which is optionally substituted with one or two groups independently selected from halogen, nitro, trifluoromethyl, cyano, hydroxy, $(C_1-C_6)$alkyl, amino, or mono- or di$(C_1-C_6)$ alkylamino; or $OR_7$, $O(CH_2)_nC(O)R_7$, $O(CH_2)_nNR_7R_8$, $O(CH_2)_nCO_2R_7$, $NR_7COR_8$, $COR_7$, $CONR_7R_8$ or $CO_2R_7$ where n=1, 2, 3, or 4; and $R_7$ and $R_8$ are the same or different and represent hydrogen, $SO_2Me$, or $(C_1-C_6)$alkyl; or $R_7$ and $R_8$ together with the nitrogen to which they are attached form a 5, 6 or 7 membered carbocyclic ring where up to two of the members are optionally hetero atoms selected from oxygen, sulfur and nitrogen, and where each member is optionally substituted with $(C_1-C_6)$alkyl;

X represents a bond or $CH_2$, where the $CH_2$ is optionally mono- or disubstituted with a $(C_1-C_6)$alkyl or $(C_1-C_6)$ alkoxy; and A, B, C and D are the same or different a represent $CR_p$ or N where $R_p$ represents hydrogen or $C_1-C_6$ alkyl or $C_1-C_6$ alkoxy where the alkyl portion of each is optionally substituted with carboxy, halogen, amino, or mono- or di$(C_1-C_6)$alkylamino, with the proviso that not more than two of A, B, C and D represent N.

2. A compound of the formula:

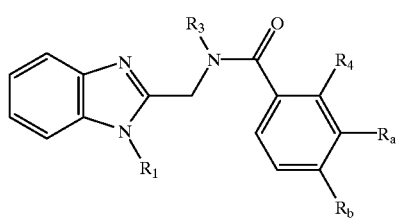

or pharmaceutically acceptable non-toxic salts thereof wherein $R_1$ is not 3-fluorobenzyl and represents (i) $(C_2-C_6)$alkenyl; or (ii) $R_1$ represents aryl$(C_1-C_6)$alkyl or heteroaryl $(C_1-C_6)$alkyl, where the ring portion of each is optionally substituted with one, two or three groups independently selected from halogen, nitro, trifluoromethyl, trifluoromethoxy, cyano, hydroxy, $(C_1-C_6)$alkyl, hydroxy$(C_1-C_6)$alkyl, amino, mono- or di$(C_1-C_6)$alkylamino, amino$(C_1-C_6)$alkyl, mono- or di$(C_1-C_6)$alkylamino$(C_1-C_6)$alkyl, mono- or di$(C_1-C_6)$alkylamino$(C_1-C_6)$alkoxy, or (iii) $OR_7$, $O(CH_2)_nC(O)R_7$, $O(CH_2)_nNR_7R_8$, $O(CH_2)_nCO_2R_7$, $NR_7COR_8$, $COR_7$, $CONR_7R_8$ or $CO_2R_7$ where n=1, 2, 3, or 4 and $R_7$ and $R_8$ are the same or different and represent hydrogen, $SO_2Me$, or $(C_1-C_6)$alkyl; or $R_7$ and $R_8$ together with the nitrogen to which they are attached form a 5, 6 or 7 membered carbocyclic ring where up to two of the members in the ring are optionally hetero atoms selected from oxygen, sulfur and nitrogen, and where each member is optionally substituted with $(C_1-C_6)$alkyl;

$R_3$ is $C_3-C_6$alkyl;

$R_4$ is chloro or fluoro; and $R_a$ and $R_b$ independently represent hydrogen or $C_1-C_6$ alkoxy.

3. A compound according to claim 2, wherein $R_1$ is benzyl mono- or disubstituted on the ring portion with $(C_1-C_6)$alkyl, halogen, nitro, trifluoromethyl, trifluoromethoxy, cyano, hydroxy, $(C_1-C_6)$alkyl, hydroxy$(C_1-C_6)$alkyl, amino, mono- or di$(C_1-C_6)$ alkylamino, aminomethyl, mono- or di$(C_1-C_6)$ alkylamino$(C_1-C_6)$alkyl, or mono- or di$(C_1-C_6)$ alkylamino$(C_1-C_6)$alkoxy; or $OR_7$, $O(CH_2)_nC(O)R_7$, $O(CH_2)_nNR_7R_8$, $O(CH_2)_nCO_2R_7$, $NR_7COR_8$, $COR_7$, $CONR_7R_8$ or $CO_2R_7$ where n=1, 2, 3, or 4; and $R_7$ and $R_8$ are the same or different and represent hydrogen, $SO_2Me$, or $(C_1-C_6)$alkyl; or $R_7$ and $R_8$ together with the nitrogen to which they are attached form a 5, 6 or 7 membered carbocyclic ring where up to two of the members are optionally hetero atoms selected from oxygen, sulfur and nitrogen, and where each member is optionally substituted with $(C_1-C_6)$alkyl;

except that $R_1$ is not 3-fluorobenzyl.

4. A compound according to claim 2, wherein $R_4$ is chloro and each of $R_a$ and $R_b$ are $C_1-C_6$ alkoxy.

5. A compound according to claim 2, wherein $R_3$ is isoamyl and $R_a$ and $R_b$ are methoxy.

6. A compound according to claim 2, wherein $R_4$ is chloro, $R_3$ is isoamyl and $R_a$ and $R_b$ are methoxy.

7. A compound according to claim 2 wherein $R_1$ is benzyl substituted in the 2- or 3-positions of its phenyl ring with hydroxy, $C_1-C_2$ alkyl, $C_1-C_2$ alkoxy, ω-[4-(($C_1-C_6$)alkyl) piperazinyl] $(C_1-C_4)$alkoxy, methyl sulfonate, 3-halopropoxy, carboxymethoxy, 2-, 3-, or 4-pyridylmethyl, 3-pyrrolidinyl$(C_1-C_6)$alkoxy, tetrazolyl, halogen, preferably bromo, fluoro or chloro, $(C_1-C_6)$alkylamino$(C_1-C_6)$alkoxy, 3-morpholin-4-yl$(C_1-C_6)$alkoxy, ω-piperidyl $(C_1-C_4)$ alkoxy, $(C_1-C_3)$alkoxycarbonylmethoxy, [N-(methylsulfonyl)carbamoyl]methoxy, trifluoromethyl, and nitro.

8. A compound according to claim 7, wherein $R_1$ is a benzyl group substituted in the 2-position of the phenyl ring.

9. A compound according to claim 2, wherein $R_1$ is 2-fluoro-, 2-bromo- or 2-chloro-5-nitrobenzyl, 3,5-dihalobenzyl where the halogen is chloro or fluoro, 5-hydroxy$(C_1-C_2)$alkyl-2-$(C_1-C_3)$alkoxybenzyl, 5-$(C_2-C_4)$ alkanoyl-2-$(C_1-C_3)$alkoxybenzyl, and 3-amino-5- or 6-$(C_1-C_2)$alkoxybenzyl.

10. A compound according to claim 2, wherein $R_1$ is alkenyl groups such as allyl or 1-buten-2- or 3-yl.

11. A compound according to claim 1 which is:

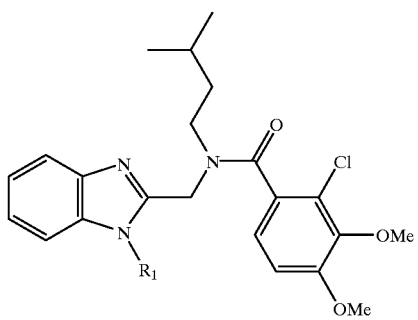

wherein:

R$_1$ represents aryl(C$_1$–C$_6$)alkyl or heteroaryl(C$_1$–C$_6$) alkyl, where the ring portion of each is optionally substituted with one, two or three groups independently selected from halogen, nitro, trifluoromethyl, trifluoromethoxy, cyano, hydroxy, (C$_1$–C$_6$)alkyl, hydroxy(C$_1$–C$_6$)alkyl, amino, mono- or di(C$_1$–C$_6$) alkylamino, aminomethyl, methylamino(C$_1$–C$_6$)alkyl, mono- or di(C$_1$–C$_6$)alkylaminomethyl, mono- or di(C$_1$–C$_6$)alkylamino(C$_1$–C$_6$)alkoxy, or OR$_7$, O(CH$_2$)$_n$C(O)R$_7$, O(CH$_2$)$_n$NR$_7$R$_8$, O(CH$_2$)$_n$CO$_2$R$_7$, NR$_7$COR$_8$, COR$_7$, CONR$_7$R$_8$ or CO$_2$R$_7$ where n=1, 2, 3, or 4 and R$_7$ and R$_8$ are the same or different and represent hydrogen, SO$_2$Me, or (C$_1$–C$_6$)alkyl or R$_7$ and R$_8$ together with the nitrogen to which they are attached form a 5, 6 or 7 membered carbocyclic ring up to two of which members are optionally hetero atoms selected from oxygen, sulfur and nitrogen, and each member is optionally substituted with (C$_1$–C$_6$)alkyl, with the proviso that R$_1$ is not 3-fluorobenzyl.

12. A compound according to claim 1 which is:

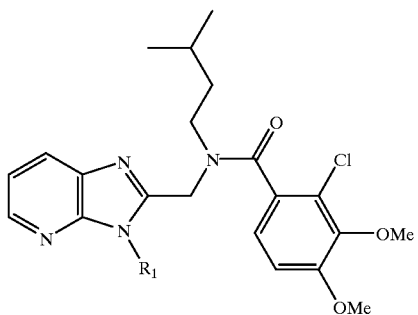

or the pharmaceutically acceptable non-toxic salts thereof wherein:

R$_1$ represents (C$_1$–C$_6$)alkenyl; or

R$_1$ represents aryl(C$_1$–C$_6$)alkyl or heteroaryl(C$_1$–C$_6$) alkyl, where the ring portion of each is optionally substituted with one, two or three groups independently selected from halogen, nitro, trifluoromethyl, trifluoromethoxy, cyano, hydroxy, (C$_1$–C$_6$)alkyl, hydroxy(C$_1$–C$_6$)alkyl, amino, mono- or di(C$_1$–C$_6$) alkylamino, aminomethyl, methylamino(C$_1$–C$_6$)alkyl, mono-or di(C$_1$–C$_6$)alkylaminomethyl, mono- or di(C$_1$–C$_6$)alkylamino(C$_1$–C$_6$)alkoxy, or OR$_7$, O(CH$_2$)$_n$C(O)R$_7$, O(CH$_2$)$_n$NR$_7$R$_8$, O(CH$_2$)$_n$CO$_2$R$_7$, NR$_7$COR$_8$, COR$_7$, CONR$_7$R$_8$ or CO$_2$R$_7$ where n=1, 2, 3, or 4 and R$_7$ and R$_8$ are the same or different and represent hydrogen, SO$_2$Me, or (C$_1$–C$_6$)alkyl or R$_7$ and R$_8$ together with the nitrogen to which they are attached form a 5, 6 or 7 membered carbocyclic ring up to two of which members are optionally hetero atoms selected from oxygen, sulfur and nitrogen, and each member is optionally substituted with (C$_1$–C$_6$)alkyl, with the proviso that R$_1$ is not 3-fluorobenzyl.

13. A compound according to claim 1, which is (2-chloro-3,4-dimethoxyphenyl)-N-({1-[(2-methoxyphenyl)methyl]benzimidazol-2-yl}methyl)-N-(3-methylbutyl) carboxamide.

14. A compound according to claim 1, which is (2-chloro-3,4-dimethoxyphenyl)-N-(3-methylbutyl)-N-{[1-({2-[3-(4-methylpiperazinyl)propoxy]phenyl}methyl)benzimidazol-2-yl]methyl}carboxamide.

15. A compound according to claim 1, which is 2-{2-[(2-{[(2-chloro-3,4-dimethoxyphenyl)-N-(3-methylbutyl) carbonylamino] methyl}benzimidazolyl)methyl]phenoxy}acetic acid.

16. A compound according to claim 1, which is (2-chloro-3,4-dimethoxyphenyl)-N-(3-methylbutyl)-N-{[3-(2-pyridylmethyl)imidazolo[5,4-b]pyridin-2-yl]methyl}carboxamide.

17. A compound according to claim 1, which is 2-(2-chlorophenyl)-N-({3-[(2-methoxyphenyl)methyl]imidazolo[5,4-b]pyridin-2-yl}methyl)-N-(3-methylbutyl) acetamide.

18. A compound according to claim 1, which is [2-chloro-4-(methylethoxy)phenyl]-N-({3-[(2-methoxyphenyl)methyl]imidazolo[5,4-b]pyridin-2-yl}methyl)-N-(3-methylbutyl)carboxamide.

19. A compound according to claim 1, which is (2-chloro-3,4-dimethoxyphenyl)-N-({1-[(2-methoxyphenyl)methyl]imidazolo[4,5-c]pyridin-2-yl}methyl)-N-(3-methylbutyl) carboxamide.

20. A compound according to claim 1, which is (2-chloro-3,4-dimethoxyphenyl)-N-(3-methylbutyl)-N-[(1-{[3-(3-pyrrolidinylpropoxy)phenyl]methyl}benzimidazol-2-yl)methyl]carboxamide.

21. A compound according to claim 1, which is (2-chloro-3,4-dimethoxyphenyl)-N-(3-methylbutyl)-N-[(1-prop-2-enylbenzimidazol-2-yl)methyl]carboxamide.

22. A compound according to claim 1, which is 2-(2-([(2-chloro-3,4-dimethoxyphenyl)-N-(3-methylbutyl) carbonylamino]methyl-1-[(2-methoxyphenyl)methyl] benzimidazol-4-yloxy) acetic acid.

23. A compound according to claim 1, which is 2-{2-[(2-{[(2-chloro-3,4-dimethoxyphenyl)-N-(3-methylbutyl) carbonylamino]methyl}benzimidazolyl)methyl]phenoxy}-N-(methylsulfonyl) acetamide.

24. A compound according to claim 1, which is (2-chloro-3,4-dimethoxyphenyl)-N-(3-methylbutyl)-N-({1-[(2-(2H-1,2,3,4-tetraazol-5-yl)phenyl)methyl]benzimidazol-2-yl}methylcarboxamide.

25. A compound according to claim 1, which is 2-(2-chlorophenyl)-N-({1-[(2-chlorophenyl)methyl] benzimidazol-2-yl}methyl)-N-pentylacetamide.

26. A compound according to claim 1, which is 2-(2-chlorophenyl)-N-({1-[(2-chlorophenyl)methyl] benzimidazol-2-yl}methyl)-N-(3-methylbutyl)acetamide.

27. A compound according to claim 1, which is (2-chloro-3,4-dimethoxyphenyl)-N-({1-[(2-methoxy-5-nitrophenyl) methyl]benzimidazol-2-yl}methyl)-N-(3-methylbutyl) carboxamide.

28. A compound according to claim 1, which is 2-chloro-3,4-dimethoxyphenyl)-N-({1-[(2-methoxyphenyl)methyl] benzimidazol-2-yl}methyl)-N-pentylcarboxamide.

29. A compound according to claim 1, which is N-({3-[(3,5-dichlorophenyl)methyl]imidazolo[5,4-b]pyridin-2- yl}methyl)(2-chloro-3,4-dimethoxyphenyl)-N-(3-methylbutyl)carboxamide.

30. A compound according to claim 1, which is (2-chloro-3,4-dimethoxyphenyl)-N-({1-[(2-hydroxyphenyl)methyl]benzimidazol-2-yl}methyl)-N-(3-methylbutyl) carboxamide.

31. A compound according to claim 1, which is 2-[(2-{[(2-chloro-3,4-dimethoxyphenyl)-N-(3-methylbutyl)carbonylamino]methyl}benzimidazolyl)methyl]phenyl methylsulfonate.

32. A compound according to claim 1, which is (2-chloro-3,4-dimethoxyphenyl)-N-[(1-{[5-(hydroxyethyl)-2-methoxyphenyl]methyl}benzimidazol-2-yl)methyl]-N-(3-methylbutyl) carboxamide.

33. A compound according to claim 1, which is N-({1-[(5-acetyl-2-methoxyphenyl)methyl]benzimidazol-2-yl}methyl)(2-chloro-3,4-dimethoxyphenyl)-N-(3-methylbutyl)carboxamide.

34. A compound according to claim 1, which is (2-chloro-3,4-dimethoxyphenyl)-N-({1-[(2-chlorophenyl)methyl]benzimidazol-2-yl}methyl)-N-(3-methylbutyl)carboxamide.

35. A compound according to claim 1, which is (2-chloro-3,4-dimethoxyphenyl)-N-([1-({3-[3-(methylamino)propoxy]phenyl}methyl)benzimidazol-2-yl]methyl}-N-(3-methylbutyl)carboxamide.

36. A compound according to claim 1, which is (2-chloro-3,4-dimethoxyphenyl)-N-(3-methylbutyl)-N-{[1-({3-[3-(4-methylpiperazinyl)propoxy]phenyl}methyl)benzimidazol-2-yl]methyl}carboxamide.

37. A compound according to claim 1, which is (2-chloro-3,4-dimethoxyphenyl)-N-(3-methylbutyl)-N-{[1-(2-pyridylmethyl)benzimidazol-2-yl]methyl}carboxamide.

38. A compound according to claim 1, which is (2-chloro-3,4-dimethoxyphenyl)-N-{[1-({3-[2-(ethylamino)ethoxy]phenyl}methyl)benzimidazol-2-yl]methyl})-N-(3-methylbutyl)carboxamide.

39. A compound according to claim 1, which is (2-chloro-3,4-dimethoxyphenyl)-N-({1-[(2-fluorophenyl)methyl]benzimidazol-2-yl}methyl)-N-(3-methylbutyl)carboxamide.

40. A compound according to claim 1, which is N-butyl (2-chloro-3,4-dimethoxyphenyl)-N-({1-[(2-methoxyphenyl)methyl]benzimidazole-2-yl}methyl)carboxamide.

41. A compound according to claim 1, which is (2-chloro-3,4-dimethoxyphenyl)-N-({3-[(3-chlorophenyl)methyl]imidazolo[5,4-b]pyridin-2-yl}methyl)-N-(3-methylbutyl)carboxamide.

42. A compound according to claim 1, which is (2-chloro-3,4-dimethoxyphenyl)-N-(3-methylbutyl)-N-({1-[(2-methylphenyl)methyl]benzimidazol-2-yl}methyl)carboxamide.

43. A compound according to claim 1, which is (2-chloro-3,4-dimethoxyphenyl)-N-(3-methylbutyl)-N-[(1-{[3-(3-morpholin-4-ylpropoxy)phenyl]methyl}benzimidazol-2-yl)methyl]carboxamide.

44. A compound according to claim 1, which is (2-chloro-3,4-dimethoxyphenyl)-N-(3-methylbutyl)-N-{[1-({3-[2-(4-methylpiperazinyl)ethoxy]phenyl}methyl)benzimidazol-2-yl]methyl}carboxamide.

45. A compound according to claim 1, which is 3-[(2-{[(2-chloro-3,4-dimethoxyphenyl)-N-(3-methylbutyl)carbonylamino]methyl}benzimidazolyl)methyl]phenyl methylsulfonate.

46. A compound according to claim 1, which is (2-chloro-3,4-dimethoxyphenyl)-N-(3-methylbutyl)-N-[(1-{[3-(2-piperidylethoxy)phenyl]methyl}benzimidazol-2-yl)methyl] carboxamide.

47. A compound according to claim 1, which is (2-chloro-3,4-dimethoxyphenyl)-N-({1-[(3-hydroxyphenyl)methyl]benzimidazol-2-yl}methyl)-N-(3-methylbutyl)carboxamide.

48. A compound according to claim 1, which is ethyl 2-{2-[(2-{[(2-chloro-3,4-dimethoxyphenyl)-N-(3-methylbutyl)-carbonylamino]methyl}benzimidazolyl)methyl]phenoxy}acetate.

49. A compound according to claim 1, which is (2-chloro-3,4-dimethoxyphenyl)-N-({3-[2-methoxyphenyl)methyl]imidazolo[5,4-b]pyridin-2-yl}methyl)-N-(3-methylbutyl)carboxamide.

50. A compound according to claim 1, which is N-({1-[(3-amino-6-methoxyphenyl)methyl]benzimidazol-2-yl}methyl)(2-chloro-3,4-dimethoxyphenyl)-N-(3-methylbutyl)carboxamide.

51. A compound according to claim 1, which is (2-chloro-3,4-dimethoxyphenyl)-N-(3-methylbutyl)-N-{[1-({2-[2-(4-methylpiperazinyl)ethoxy]phenyl}methyl)benzimidazol-2-yl]methyl}carboxamide.

52. A compound according to claim 1, which is N-butyl (2-chloro-3,4-dimethoxyphenyl)-N-({1-[(3-fluorophenyl)methyl]benzimidazol-2-yl}methyl)carboxamide.

53. A compound according to claim 1, which is (2-chloro-3,4-dimethoxyphenyl)-N-(3-methylbutyl)-N-[(1-{[2-(trifluoromethyl)phenyl]methyl}benzimidazol-2-yl)methyl] carboxamide.

54. A compound according to claim 1, which is [2-chloro-4-(methylethoxy)phenyl]-N-(3-methylbutyl)-N-({1-[(2-nitrophenyl)methyl]benzimidazol-2-yl}methylcarboxamide.

55. A compound according to claim 1, which is (2-chloro-3,4-dimethoxyphenyl)-N-[(4-methyoxy-1-prop-2-enylbenzimidazol-2-yl)methyl]-N-(3-methylbutyl) carboxamide.

56. A pharmaceutical composition comprising a compound according to claim 1 and a pharmaceutically acceptable carrier or excipient.

\* \* \* \* \*